United States Patent [19]

Fiel

[11] Patent Number: 5,236,915

[45] Date of Patent: Aug. 17, 1993

[54] MESO POLY(4-SULFONATOPHENYL) PORPHINES AS MRI IMAGE ENHANCING AGENTS

[75] Inventor: Robert J. Fiel, Williamsville, N.Y.

[73] Assignee: Health Research, Inc., Buffalo, N.Y.

[21] Appl. No.: 531,113

[22] Filed: May 31, 1990

[51] Int. Cl.$^5$ .................... A61K 31/555; A61K 31/40
[52] U.S. Cl. ................................. 514/185; 514/410; 540/145
[58] Field of Search ................. 514/185, 410; 540/145

[56] References Cited

U.S. PATENT DOCUMENTS 5,010,073  4/1991  Kappas et al. .................... 514/185

FOREIGN PATENT DOCUMENTS 3809671  9/1989  Fed. Rep. of Germany .......... 424/9

OTHER PUBLICATIONS

Okura, et al Chemical Abstracts vol. 97, 1982, Abstract 41391z.
"Paramagnetic Metalloporphyrins as Potential Contrast Agents in NMR Imaging", Chen et al., Mar. 1984, *FEBS Letters*, pp. 70-74.
"Metalloporphyrin Contrast Agents for Magnetic Resonance Imaging of Human Tumors in Mice", Patronas et al., Mar. 1986, *Cancer Treatment Reports*, vol. 70, No. 3, pp. 391-395.
"Proton Relaxation Enhancement by Manganese (III) TPPS$_4$ in a Model Tumor System", Fiel et al., 1987, *Magnetic Resonance Imaging*, pp. 149-156.

(List continued on next page.)

*Primary Examiner*—Donald G. Daus
*Assistant Examiner*—E. C. Ward
*Attorney, Agent, or Firm*—Michael L. Dunn; Mark G. Bloom; James F. Mudd

[57] ABSTRACT

A chelated compound of the formula:

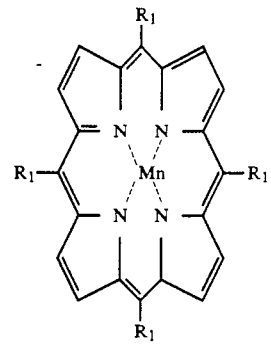

where $R_1$ is independently at each occurrence,

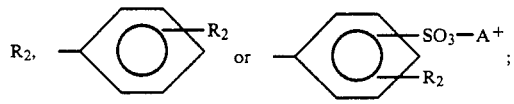

$R_2$ is independently at each occurrence hydrogen, lower alkyl, lower alkyl ester, lower alkyl ether, hydroxy or halogen; A is H, Li, Na, Ca+, Mg+ or Zn+; and Mn is trivalent manganese; provided that, at least two and no more than three $R_1$ radicals are

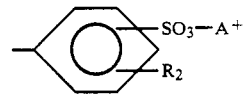

The compound of the invention is particularly suitable for use in a physiologically compatible composition comprising a physiologically compatible liquid carrier for magnetic resonance imaging. The compound is also suitable as a chelate for removal of manganese from a system.

The invention also comprises a method for enhanced magnetic imaging of a mammal organism which comprises introducing the composition at a level of from 20 to 200 mg/Kg of body weight into the circulatory system of the organism; and making a magnetic resonance image of at least a portion of said organism at from 30 minutes to 36 hours after said introduction.

6 Claims, 2 Drawing Sheets

OTHER PUBLICATIONS

"Metalloporphyrin Contrast Enhancement of Tumors in Magnetic Resonance Imaging", Ogan et al., Oct. 1987, *Investigative Radiology*, vol. 22, ppp. 822-828.

"Metalloporphyrin Enhancement of Magnetic Resonance Imaging of Human Tumor Xenografts in Nude Mice", Furmanski et al., Aug. 15, 1988, *Cancer Research*, pp. 4604-4610.

"Mechanism of the Localization of Manganese (III) Mesotetra (4-Sulfonatophenyl) Porphine in Mice Bearing L1210 Tumors", Fiel et al., 1988, *Cancer Letters*, pp. 23-32.

"Isointense Model for the Evaluation of Tumor-Specific MRI Contrast Agents", Button et al., 1988, *Magnetic Resonance Imaging*, vol. 6, pp. 275-280.

Megnin et al., Biochim. et Biophys. Acta 929: 173-181 (1987).

Fiel R. J., Journal of Biomolecular Structure and Dynamics, ISSN 0739-1102, vol. 6, Issue No. 6 (1989).

Henkelman R. M. et al., Magnetic Resonance in Medicine 4, 61-66 (1987).

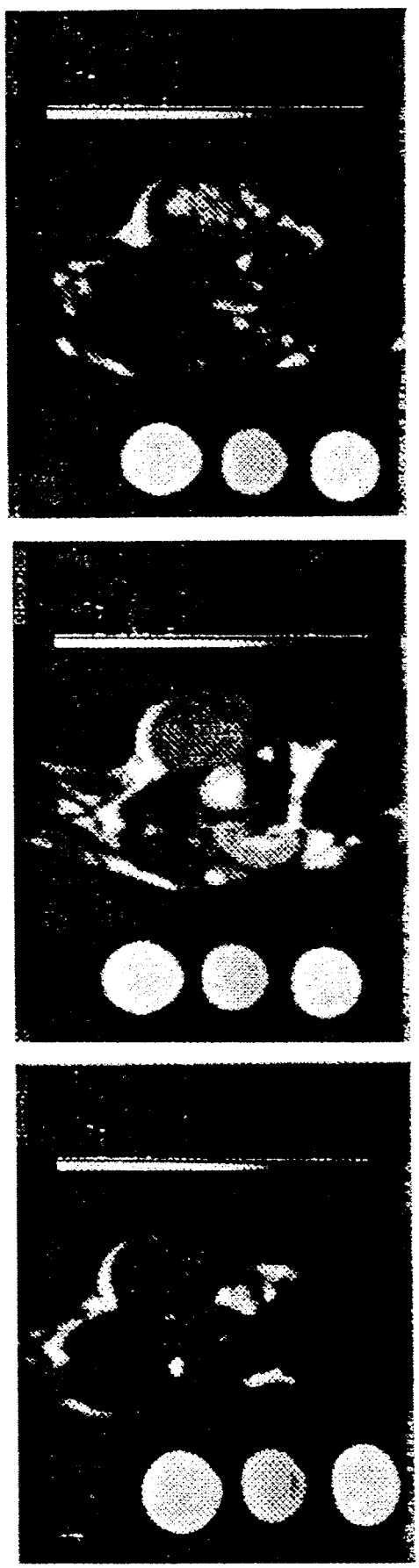

MESO POLY(4-SULFONATOPHENYL) PORPHINES AS MRI IMAGE ENHANCING AGENTS

BACKGROUND OF THE INVENTION

This invention relates generally to magnetic resonance imaging (MRI) and more particularly to MRI using ligands as contrast agents.

For several years, magnetic resonance imaging (MRI) has been proposed as a valuable aid in diagnosing and locating malignant tumors. It has, for example, been known that certain paramagnetic metal ions localize in malignant tumors and decrease the relaxation time of hydrogen ions present in water there. Nevertheless, the use of metal ions as contrast agents has been hampered by their inherent high toxicity.

Recently, it has been found that porphyrin and many of its derivatives also localize in malignant tumors. Unfortunately, free porphyrins do not sufficiently increase the relaxation time of water to be effective MRI contrast agents.

Metalloporphyrins have, to some extent, been used to achieve higher contrast on X-rays of neoplastic tissue. One difficulty observed with the use of metalloporphyrins in this context has been the tendency of some metalloporphyrins to dissociate and release the highly toxic metal ion. Additionally, it is noted that the characteristics of a suitable X-ray image enhancer and a suitable magnetic resonance image enhancer are quite different.

It has, however, been proposed that manganese III meso-tetra(4-sulfonatophenyl)porphine (TPPS$_4$) could be used as a magnetic resonance image enhancer for the deletion of tumors. While such a compound had certain advantages over previous enhancers, the toxicity, tumor uptake, tumor localization and relaxation time were still not as good as desired.

BRIEF DESCRIPTION OF THE DRAWINGS

FIG. 2 shows coronal sections (2.5 mm) of tumor bearing mouse. Control (upper left), 1 hour post injection (100 mg/kg) of Mn(III)TPPS$_3$ (upper right), and 24 hours post injection (lower left). Note concentration of porphyrin in kidneys at 1 hour (arrow) and heterogeneous signal enhancement in tumor at 24 hours. Image intensity working standards (top to bottom) 28 mM CuSO$_4$ in 1 N HCl, 5 mM GdDTPA in isotonic saline and baby oil.

BRIEF DESCRIPTION OF THE INVENTION

Figure 1:
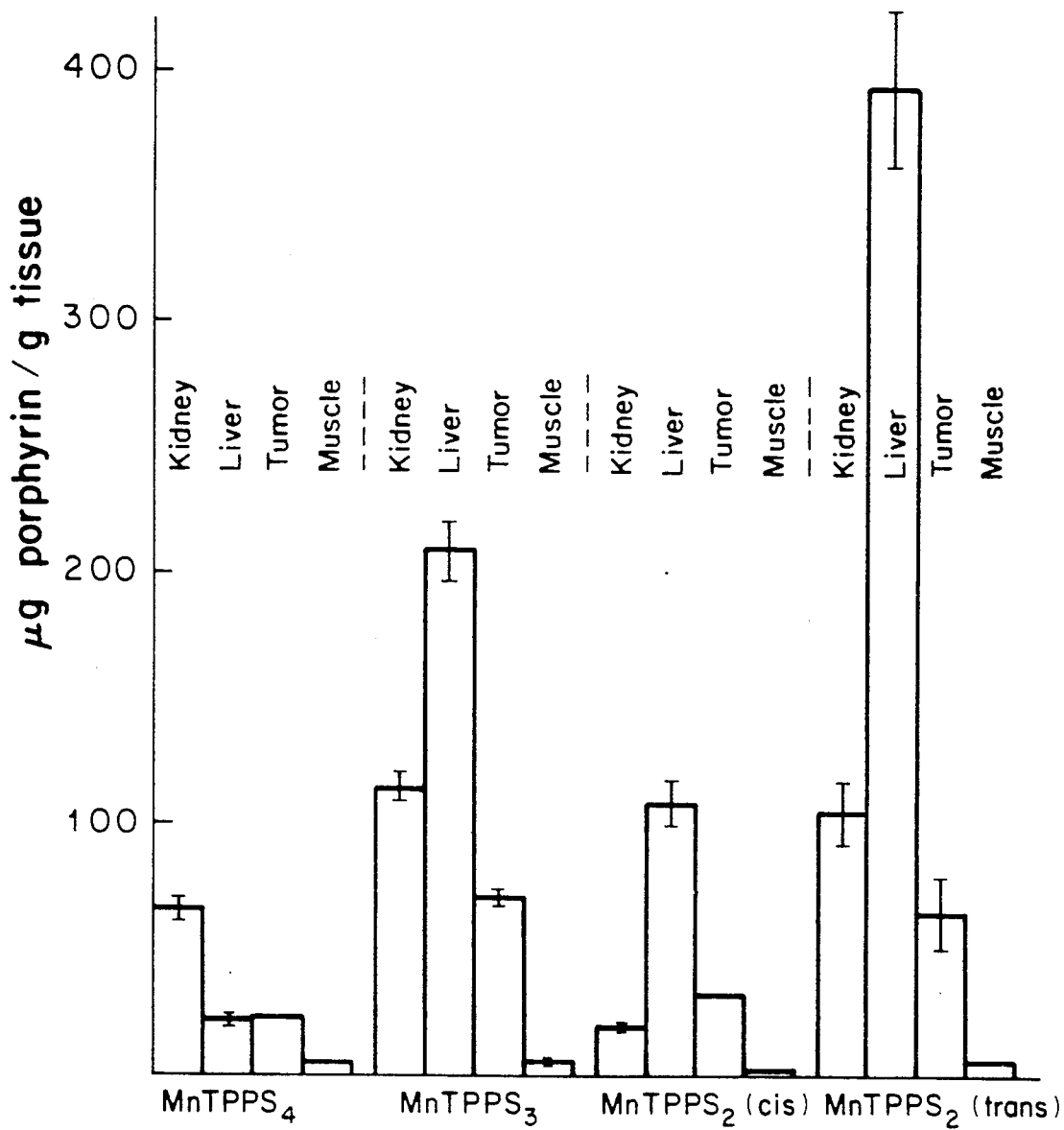
FIG. 1 shows concentration of porphyrin (as indicated) in each of four tissues excised and analyzed at 24 hours post-injection (i.v.). Measured concentrations are averages for two mice.

In accordance with the present invention, there is provided a chelated compound of the formula:

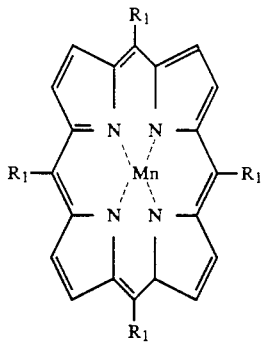

where R$_1$ is independently at each occurrence,

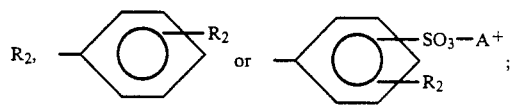

R$_2$ is independently at each occurrence hydrogen, lower alkyl, lower alkyl ester, lower alkyl ether, hydroxy or halogen; A is H, Li, Na, Ca+, Mg+ or Zn+; and Mn is trivalent manganese; provided that, at least two and no more than three R$_1$ radicals are

The compound of the invention is particularly suitable for use in a physiologically compatible composition comprising a physiologically compatible liquid carrier for magnetic resonance imaging. The compound is also suitable as a chelate for removal of manganese from a system.

The invention also comprises a method for enhanced magnetic imaging of a mammal organism which comprises:

1. introducing the composition at a level of from 20 to 200 mg/Kg of body weight into the circulatory system of the organism; and
2. making a magnetic resonance image of at least a portion of said organism at from 30 minutes to 36 hours after said introduction.

The method is an improvement over prior methods since localization in tumors and relaxation time are enhanced thus better images can be obtained at lower dosage levels. Further, the toxicity of the compound of the invention is lower as for example compared with manganese III meso—tetra 4-sulfonatophenyl porphine (MnTPPS$_4$).

DETAILED DESCRIPTION OF THE INVENTION

The compound of the invention is intended to include any manganese III meso-phenyl porphine containing two to four phenyl groups wherein at least two and no more than three of the phenyl groups are sulfonated and wherein the compound is more water soluble than manganese III meso-[(4-sulfonatophenyl)triphenyl] porphine and less water soluble than manganese III meso-tetra 4-sulfonatophenyl porphine. Essentially any substituent can be added to the phenyl groups provided that they do not render the compound too toxic to use in vivo for magnetic resonance imaging or alter the water solubility so that it is outside of the limits above described. In general, tetra sulfonated compounds are too water soluble and the monosulfonated compounds are insufficiently water soluble. The compounds of the invention as described in this paragraph shall be referred to in this specification as "solubility balanced manganese III sulfonated mesophenyl porphines"

Examples of substituents which may be attached to the phenyl groups, or to the $R_1$ position on the structural formula shown above, include hydrogen, lower alkyl, e.g., methyl, ethyl, propyl and butyl; lower alkyl ester, e.g., methylene acetate, ethylene acetate; lower alkylether, e.g., ethylene methyl ether, methylene ethyl ether, methylene propyl ether, propylene ethyl ether; hydroxy; or halogen, e.g., fluorine, chlorine, bromine and iodine. More than one such substituent can be added to each phenyl group provided that, the toxicity characteristics and solubility characteristics are not adversely affected as previously discussed.

In general, the compounds should be less toxic than manganese III meso-tetra 4 sulfonatophenyl porphine at concentrations which result in magnetic resonance images of similar quality. For example, $MnTPPS_4$ showed an $LD_{50}$ for L1210 cells in culture at day 2 of 674 mg/ml, while $MnTPPS_3$ showed an $LD_{50}$ for L1210 cells under the same conditions of 1010 mg/ml.

The preferred chelated compounds in accordance with the present invention are the acids and ionic salts of manganese III meso—[tri (4—sulfonatophenyl) phenyl] porphine ($MnTPPS_3$); manganese III meso—[trans—di(4—sulfonato-phenyl) diphenyl] porphine (trans $MnTPPS_2$); manganese III meso—[cis—di (4-sulfonatophenyl) diphenyl] porphine (cis $MnTPPS_2$); and mixtures thereof. In general, the most preferred single compound is the manganese III chelate of meso - [tri (4 - sulfonatophenyl) phenyl porphine.

These compounds are suitable as chelates for removing manganese from chemical systems and are especially preferred for use in conjunction with magnetic resonance imaging of biological systems, e.g., mammals.

In using the compounds, they are dissolved in a physiologically compatible liquid and introduced into the organisms. The preferred method of introduction is parenterally, especially intravenously; although in certain circumstances for special imaging problems, e.g., of the digestive tract, ingestion is possible.

The physiologically compatible liquid is usually normal saline solution which is sufficiently pure to prevent an adverse physiologic reaction. Other physiologically compatible fluids such as glycerin or propylene glycol may be used or included.

Usually from about 0.1 to about 1.0 weight percent of the chelate is dissolved in the fluid.

The method for enhancing magnetic resonance imaging of a mammal comprises introducing the manganese chelate porphine compound at a level of from 20 to 200 mg/Kg of body weight into the circulatory system of the organism and making a magnetic resonance image of at least a portion of said organism at from 30 minutes to 36 hours after the introduction.

The most preferred level of introduction is from 30 to 100 mg/Kg of body weight and the most preferred time period for imaging is from 12 to 30 hours.

Any suitable magnetic resonance imaging equipment may be used, as is apparent to one skilled in the art. In general, for use in accordance with the present invention, the magnetic transmitting and receiving coil is tuned to about 15 MHz. Any suitable clinical scanner may be used. Examples.

The free base porphyrins, meso-tetra(4-sulfonatophenyl) porphine ($TPPS_4$), meso-[tri(4-sulfonatophenyl)-phenyl]porphine ($TPPS_3$), meso[trans-di(4-sulfonatophenyl)diphenyl]porphine (trans-$TPPS_2$) and meso-[cis-di(4-sulfonatophenyl)di-phenyl]porphine (cis-$TPPS_2$), are known to those skilled in the art and are commercially available, for example, from Porphyrin Products, Inc. Manganese chelates were prepared in their acid form using the procedures known to those skilled in the art, e.g., Fiel et. al., Proton Relaxation Enhancement By Manganese(III)$TPPS_4$ In A Model Tumor System. Magn. Reson. Imaging 5:149-156; 1987. In general, the chelates are prepared by heating in solution with a manganese salt. The chelates were characterized by absorption spectra and, in the case of $MnTPPS_3$ and cis-$MnTPPS_2$, by mass spectroscopy. The absorption spectra of the chelates is distinct from the corresponding free bases with absorption bands at 380, 401 and 467 nm in distilled water. Three bands are also observed in the long wavelength regions i.e., 513, 565 and 598 nm for $MnTPPS_4$ and $MnTPPS_3$; 515, 567 and 599 nm for cis-$MnTPPS_2$ and trans-$MnTPPS_2$. The absorption bands are reproducible to $\pm 0.5$ nm. $MnTPPS_3$ and cis-$MnTPPS_2$ were characterized further by fast atom bombardment (positive mode) mass spectroscopy. For $MnTPPS_3$ a molecular ion was observed with a mass of 907.6 a.m.u. corresponding to $C_{44}H_{28}N_4S_3O_9Mn$ (907.045) as the sulfonic acid form. The axial anion, in our case acetate, is not observed. Similarly, a molecular ion with a mass of 828.3 a.m.u. was observed for the acid form of cis-$MnTPPS_2$, corresponding to $C_{44}H_{28}N_4S_2O_6Mn$ (827.088). Water of hydration was found to be a variable factor for all four manganese porphyrin derivatives. Stock solutions of the porphyrins were all prepared in terms of mg/ml for all measurements including those used for imaging purposes.

Relaxation and biodistribution measurements were carried out using procedures known to those skilled in the art, e.g., Fiel et. al., supra. Briefly, the longitudinal relaxation time ($T_1$) for excised tissue was measured at 37° C. with a Praxis II ™ relaxometer (Praxis Corporation, San Antonio, Tex.) operating at 10.7 MHz and employing a saturation recovery pulse sequence.

Biodistribution (liver, kidney, muscle and tumor) of the four manganese porphyrins was measured by absorption spectroscopy of ammonia/methanol mixtures and expressed as $\mu g$ metalloporphyrin per gram of tissue (wet weight). Quantitation was based upon the extinction coefficient for each porphyrin as predetermined in the extraction solutions.

SMT-F (spontaneous mammary carcinoma) was maintained in the laboratory on a biweekly schedule in which 1 $mm^3$ pieces of tumor were implanted in the flank of DBA/2HaRos-d$+Ha$ mice. Porphyrins were delivered by intravenous injection in the tail vein.

Magnetic resonance images were made using a custom-built small animal (mouse) transmitter/receiving coil similar to the design of Henkelman et al., Small Animal Imaging With A Clinical Imager. Magn. Reson. Med. 4:61-66; 1987, and tuned to 15 MHz for use with a Diasonics ™ 0.35 Tesla clinical scanner. Images were made using a TR of 500 msec. and a TE of 50 msec. with a slice thickness of 2.5 mm.

TR is the repeat time and TE is the echo time.

Images were analyzed using a Hewlett Packard Vectra TM ES/12 personal computer with high resolution VGA graphics after digitization via a Dage 70 TM camera with Vidicon tube utilizing a Matrox TM MVP AT image capture/display board. Signal intensity measurements were made from selected areas of interest (AOI) using Image-Pro II TM software (Media Cybernetics, Silver Spring, Md.). Any suitable similar apparatus and software can of course be used. Generally an entire section (image slice) of tumor was circumscribed using a free-form area of interest option. The area of interest was then represented by a histogram relating pixel frequency to gray level. Each gray level (0-255) was multiplied by its associated frequency. The resulting products were summed and divided by the area of interest in units of centimeter squared. The procedure was repeated three times to determine a mean value for the tumor at each time period. The same procedure was carried out for the midrange working standard (5 mM Gd DTPA).

Results

The distribution of each porphyrin in kidney, liver, muscle and tumor was determined at 1 and 24 hours post injection. The data taken at 24 hours are shown in FIG. 1. Measurable concentrations of each porphyrin were found in all tissues tested. Viewed from the perspective of total uptake, i.e., the sum of the concentration of porphyrin in four tissues, the relative order is $MnTPPS_2(trans) > MnTPPS_3 > MnTPPS_2(cis) > MnTPPS_4$, and the ratio, normalized to $MnTPPS_2(trans)$, is 1.0:0.6:0.4:0.2, respectively. The large value for total uptake expressed by $TPPS_2(trans)$ is due in part to its high affinity for liver in which its concentration is approximately twice that of the next highest porphyrin, $MnTPPS_3$. The effect of the hydrophobicity of the porphyrins on uptake in liver is illustrated in table 1 where the liver/kidney ratios are shown to be smallest for $MnTPPS_4$, the least hydrophobic porphyrin, and greatest for the $MnTPPS_2$ pair, the most hydrophobic of the series.

Porphyrin uptake into the tumor was measured and presented as a ratio of the concentration in tumor to muscle (table 2). Measurements at 1 hour show only small differences among the four porphyrins with the ratio favoring $MnTPPS_4$. At 24 hours, $MnTPPS_3$, which has the highest concentration in tumor, shows the most favorable tumor/muscle ratio, and $MnTPPS_4$ the least favorable.

Relaxivity in tumor tissue was measured for each porphyrin on excised tissue at 10.7 MHz, 24 hours post injection of a 100 mg/kg dose (table 3). Interestingly, the three more hydrophobic porphyrins (phenyl substituted) appear to have higher relaxivities than $MnTPPS_4$. The highest value was found for $MnTPPS_3$. All four porphyrins significantly enhanced the relaxation rate ($1/T_1$) of the tumor.

Of the four porphyrins examined, $MnTPPS_3$ was found to have both optimal relaxivity in tumor and the most favorable tumor/muscle ratio at 24 hours. The tumor contrast enhancing characteristics of this porphyrin are shown in FIG. 2. The control image displays a single coronal slice at the level of the kidneys. A large tumor is apparent on the right side of the mouse. The tumor mass appears to be homogeneous and approximately isointense with the kidneys. At 1 hour post injection, the tumor appears somewhat brighter than the control, although it remains homogeneous. Close examination of the kidneys shows a high intensity signal in the region of the pelvis indicating the presence of $MnTPPS_3$ in the urine, consistent with the high concentration found in the kidney at 1 hour (not shown).

At 24 hours, the tumor appears very heterogeneous. It is circumscribed by a narrow somewhat hyperintense ring and composed of a mottled hyperintense core. Microscopic examination indicated that the mottled area generally correlate with necrotic regions of the tumor. The results clearly suggest that $MnTPPS_3$ has an affinity for and the ability to concentrate in specific regions of the SMT-F tumor and delineate tumor heterogeneity.

The visual differences (intensity) noted between control and treated (FIG. 2) were quantitated using mean intensity values normalized to corresponding working standards. The results (table 4) indicate that differences between control and enhanced and between one and 24 hrs are significant. Signal intensity measured at 24 hrs is 21% higher than control and 7% higher than the value determined at 1 hr. Note that this analysis ignores the fact that the increase in intensity at 24 hrs is actually concentrated into a relatively small area of the tumor by averaging over the entire section.

Measured at 24 hours post injection, $MnTPPS_3$ demonstrates the highest concentration in the SMT-F tumor, the largest value of relaxivity (tumor) and the most favorable tumor/muscle ratio of the four porphyrin derivatives examined. At 24 hours, the signal intensity increased significantly within regions of the tumor that generally correspond to necrosis. The contrast enhancement effects, found at 1 hour in the kidney and 24 hours in the tumor, can be explained by the time dependent concentration of $MnTPPS_3$. In the case of the kidney, $MnTPPS_3$ is cleared rapidly and concentrated in the urine where it selectively enhances the medulla and pelvic structures. In the tumor, signal enhancement is seen in a heterogeneous necrotic core, but only after enough time has elapsed to allow concentration in this region (between 1 and 24 hours).

It is apparent that the manganese porphyrins of the invention are effective contrast enhancement agents. The porphyrins have significant specificity for tumor relative to muscle; $MnTPPS_3$ is superior to all others in regard to tumor uptake, tumor/muscle ratio and relaxivity in tumor tissue and cis and trans $MnTPPS_2$ are superior to $MnTPPS_4$.

TABLE 1

Ratios of the concentration of porphyrins in liver to kidney determined at 1 and 24 hours post injection.

|  | $MnTPPS_4$ | $MnTPPS_3$ | $MnTPPS_{2(trans)}$ | $MnTPPS_{2(cis)}$ |
|---|---|---|---|---|
| 1 hour | 0.3 | 0.7 | 4.4 | 6.4 |
| 24 hours | 0.3 | 1.8 | 3.8 | 5.5 |

TABLE 2

Ratios of the concentration of porphyrins in tumor to muscle determined at 1 hour and 24 hours post injection.

|  | $MnTPPS_4$ | $MnTPPS_3$ | $MnTPPS_{2(trans)}$ | $MnTPPS_{2(cis)}$ |
|---|---|---|---|---|
| 1 hour | 3.7 | 3.2 | 2.3 | 2.8 |
| 24 hours | 4.4 | 13.1 | 11.6 | 9.7 |

TABLE 3

Relaxivity at 24 hours of tumors excised from mice treated with porphyrin.

| Porphyrin (100 mg/kg) | Relaxivity* |
|---|---|
| MnTPPS$_4$ | 0.207 ± .004 |
| MnTPPS$_3$ | 0.543 ± .152 |
| MnTPPS$_{2(cis)}$ | 0.361** |
| MnTPPS$_{2(trans)}$ | 0.296 ± .045 |

*Expressed as the relaxation rate of tissue from treated animals (24 hrs) minus the relaxation rate of tissue from untreated animal (control) divided by the concentration of porphyrin in the tumor tissue.
**Measurement from one mouse.

TABLE 4

| | Normalized Signal Intensity. | | |
|---|---|---|---|
| | Control | 1 hr | 24 hrs |
| mean ± SD | 0.685 ± .015 | 0.774 ± .006 | 0.828 ± .007 |
| range | 0.652–0.701 | 0.766–0.780 | 0.820–0.836 |
| confidence interval* | 0.654–.710 | 0.769–0.784 | 0.815–0.841 |

*99% (t-test).

WHAT IS CLAIMED IS:

1. A physiologically compatible composition comprising a physiologically compatible liquid carrier and a chelated compound of the formula,

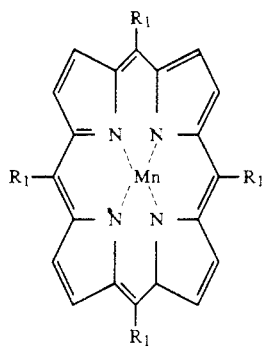

where $R_1$ is independently at each occurrence,

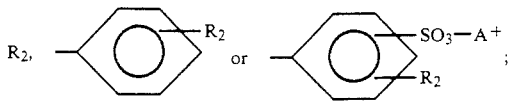

$R_2$ is independently at each occurrence hydrogen, lower alkyl, lower alkyl ester, lower alkyl ether, hydroxy or halogen; A is H, Li, Na, Ca+, Mg+ or Zn+; and Mn is trivalent manganese; provided that, at least two and no more than three $R_1$ radicals are

2. A physiologically compatible composition comprising a physiologically compatible liquid carrier and a compound selected from the manganese chelates of the group consisting of manganese III meso—[tri(4—sulfonatophenyl) phenyl] porphine; manganese III meso—[trans—di (4—sulfonato-phenyl) diphenyl] porphine; manganese III meso—[cis—di (4-sulfonatophenyl) diphenyl] porphine; and mixtures thereof.

3. A physiologically compatible composition comprising a physiologically compatible liquid carrier and the compound manganese III meso—[tri (4—sulfonatophenyl) phenyl] porphine.

4. The composition of claim 1 wherein the composition comprises from 0.1% to 1% weight percent of the chelate in normal saline.

5. The composition of claim 2 wherein the composition comprises from 0.1% to 1% weight percent of the chelate in normal saline.

6. The composition of claim 3 wherein the composition comprises from 0.1% to 1% weight percent of the chelate in normal saline.

* * * * *